(12) United States Patent
Kamei (10) Patent No.: US 9,020,226 B2
(45) Date of Patent: Apr. 28, 2015

(54) IMAGE PROCESSING APPARATUS, IMAGE PROCESSING METHOD, AND IMAGE PROCESSING PROGRAM

(75) Inventor: Toshio Kamei, Tokyo (JP)

(73) Assignee: NEC Corporation, Tokyo (JP)

( * ) Notice: Subject to any disclaimer, the term of this patent is extended or adjusted under 35 U.S.C. 154(b) by 264 days.

(21) Appl. No.: 13/816,441

(22) PCT Filed: Aug. 2, 2011

(86) PCT No.: PCT/JP2011/068010
§ 371 (c)(1),
(2), (4) Date: Feb. 11, 2013

(87) PCT Pub. No.: WO2012/020718
PCT Pub. Date: Feb. 16, 2012

(65) Prior Publication Data
US 2013/0136327 A1    May 30, 2013

(30) Foreign Application Priority Data
Aug. 12, 2010    (JP) ................................ 2010-180730

(51) Int. Cl.
*G06K 9/00*    (2006.01)
*G06T 7/00*    (2006.01)
(Continued)

(52) U.S. Cl.
CPC ............... *G06T 7/0012* (2013.01); *A61B 5/117* (2013.01); *A61B 5/1172* (2013.01); *A61B 5/489* (2013.01); *G06K 9/0008* (2013.01); *G06K 9/00892* (2013.01); *G06K 2009/0006* (2013.01); *G06K 2009/00932* (2013.01)

(58) Field of Classification Search
None
See application file for complete search history.

(56) References Cited

U.S. PATENT DOCUMENTS

2010/0278397 A1    11/2010    Tobe et al.

FOREIGN PATENT DOCUMENTS

| JP | 2007-219624 A | 8/2007 |
| JP | 2007-219625 A | 8/2007 |

(Continued)

OTHER PUBLICATIONS

Hong, Lin, Yifei Wan, and Anil Jain. "Fingerprint image enhancement: algorithm and performance evaluation." Pattern Analysis and Machine Intelligence, IEEE Transactions on 20.8 (1998): 777-789.*

(Continued)

*Primary Examiner* — John Strege
*Assistant Examiner* — Raphael Schwartz
(74) *Attorney, Agent, or Firm* — Sughrue Mion, PLLC (57) ABSTRACT

[Problem] To separate biological patterns more efficiently and effectively.
[Solution] An image processing apparatus according to the present invention is characterized by comprising: an image obtaining means for obtaining an image in which a first biological pattern and a second biological pattern having different textures are superimposed; a normalizing means for normalizing density of the image on the basis of an average and a standard deviation of pixel values inside a local region in the image using a parameter in accordance with difference in texture between the first biological pattern and the second biological pattern to thereby separate the first biological pattern and the second biological pattern in the image; and a pattern collating means for collating a known pattern for collation with each of the first biological pattern and the second biological pattern separated by the normalizing means.

10 Claims, 8 Drawing Sheets

(51) Int. Cl.
*A61B 5/117* (2006.01)
*A61B 5/00* (2006.01)

(56) References Cited

FOREIGN PATENT DOCUMENTS

| | | |
|---|---|---|
| JP | 2009-059249 A | 3/2009 |
| WO | 2010/044250 A1 | 4/2010 |

OTHER PUBLICATIONS

Wang, Lingyu, Graham Leedham, and David Siu-Yeung Cho. "Minutiae feature analysis for infrared hand vein pattern biometrics." Pattern recognition 41.3 (2008): 920-929.*

Olsen, Martin Aastrup, et al. "Contrast enhancement and metrics for biometric vein pattern recognition." Advanced Intelligent Computing Theories and Applications. Springer Berlin Heidelberg, 2010. 425-434.*

* cited by examiner

| SEX | AGE | PARAMETER FOR GAUSSIAN FILTER (e.g. KERNEL SIZE) | PARAMETER FOR NORMALIZING GRAY VALUE (e.g. EQUALIZED AREA SIZE) | |
|---|---|---|---|---|
| | | | BLOOD VESSEL | FINGERPRINT |
| MAN | CHILD | 15 | 15 | 2 |
| | ADULT | 20 | 20 | 3 |
| WOMAN | CHILD | 15 | 14 | 2 |
| | ADULT | 20 | 18 | 3 |

Fig.7

IMAGE PROCESSING APPARATUS, IMAGE PROCESSING METHOD, AND IMAGE PROCESSING PROGRAM

CROSS REFERENCE TO RELATED APPLICATIONS

This application is a National Stage of International Application No. PCT/JP2011/068010 filed Aug. 2, 2011, claiming priority based on Japanese Patent Application No. 2010-180730 filed Aug. 12, 2010, the contents of all of which are incorporated herein by reference in their entirety.

TECHNICAL FIELD

The present invention relates to a technology of separating biological patterns.

BACKGROUND ART

The patent literature 1 disclosed a technology in which it performs Fourier transform to an obtained image of a finger which is photographed and obtained, and separates into a vein pattern and a fingerprint/wrinkle pattern by a difference of partial frequency ingredient. For example, paragraph [0048] includes a description that "For the vein pattern and the fingerprint/wrinkle pattern, because partial frequency ingredients after performed Fourier transform are distributed around a low frequency side for the former pattern and is distributed around a high frequency side for the latter pattern, separations are enabled." In addition, paragraph [0064] includes a description that "It can perform a personal authentication using both of a fingerprint image and a blood vessel image. For example, it can enhance the security in the case when the fingerprint image coincides with a registered fingerprint image and when the blood vessel image coincides with a registered blood vessel image. When an authentication probability is low if the authentication is done only by an image authentication of the blood vessel image or the fingerprint image, it can reduce an error rate of the authentication by authenticating that one of the images will be coincided. In this case, a blood vessel image inputting apparatus 200 and a blood vessel image collating apparatus 300 will be apparatuses which are targeting both the fingerprint image and the blood vessel image."

PRIOR ART

Patent Literature

[Patent Literature 1] Japanese Patent Application Laid-Open No. 2007-219624

SUMMARY OF THE INVENTION

Problem to be Solved by the Invention

However, in order to perform Fourier transform, it requires huge amount of calculations and therefore it imposes a heavy load on the apparatus accordingly. In addition, the above described separation technology of the biological pattern is not enough for enhancing accuracy. In particular, the above described separation technology has a problem that it is relatively weak for any noises.

The object of the present invention is to provide a technology which settles the above described problems.

Means for Solving Problems

To achieve the object mentioned above, an apparatus according to the present invention is characterized by comprising:

an image obtaining means for obtaining an image in which a first biological pattern and a second biological pattern having different textures are superimposed;

a normalizing means for normalizing density of the image on the basis of an average and a standard deviation of pixel values inside a local region in the image using a parameter in accordance with difference in texture between the first biological pattern and the second biological pattern to thereby separate the first biological pattern and the second biological pattern in the image; and a pattern collating means for collating a known pattern for collation with each of the first biological pattern and the second biological pattern separated by the normalizing means.

To achieve the object mentioned above, a method according to the present invention is characterized in that obtaining an image in which a first biological pattern and a second biological pattern having different textures are superimposed, normalizing density of the image on the basis of an average and a standard deviation of pixel values inside a local region in the image using a parameter in accordance with difference in texture between the first biological pattern and the second biological pattern to thereby separate the first biological pattern and the second biological pattern in the image, and collating a known pattern for collation with each of the first biological pattern and the second biological pattern separated by the normalizing means.

To achieve the object mentioned above, a non-transitory computer-readable medium according to the present invention stores an image processing program, characterized by making a computer operate as:

an image obtaining means for obtaining an image in which a first biological pattern and a second biological pattern having different textures are superimposed;

a normalizing means for normalizing density of the image on the basis of an average and a standard deviation of pixel values inside a local region in the image using a parameter in accordance with difference in texture between the first biological pattern and the second biological pattern to thereby separate the first biological pattern and the second biological pattern in the image; and a pattern collating means for collating a known pattern for collation with each of the first biological pattern and the second biological pattern separated by the normalizing means.

Effect of the Invention

According to the present invention, it can more efficiently and effectively separate the biological patterns.

EXEMPLARY EMBODIMENT TO CARRY OUT THE INVENTION

Hereinafter, embodiments of the present invention will be described exemplarily and in detail with reference to the drawings. However, the components described in the following embodiments are only for exemplary descriptions, and the scope of the technology of the present invention is not limited to these.

First Embodiment

Figure 1:
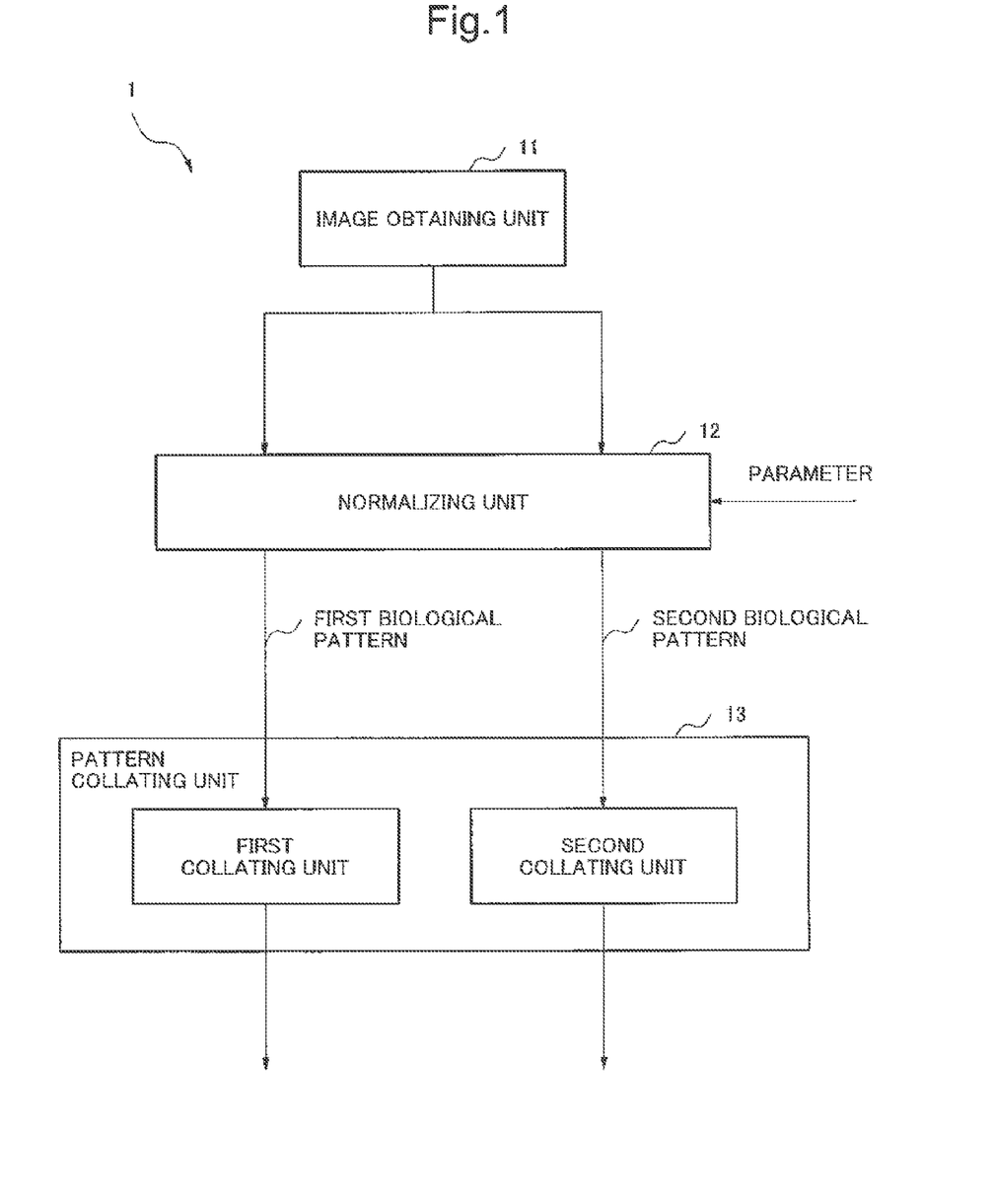
FIG. 1 is a block diagram showing a functional configuration of an image processing apparatus according to the first embodiment of the present invention.

The image processing apparatus according to the first embodiment of the present invention will be described with reference to FIG. 1. FIG. 1 indicates the exemplary configuration of an image processing apparatus 1 which authenticates a biological pattern existing in a biological apparatus. The image processing apparatus 1 includes an image obtaining unit 11 which obtains a superimposed image of the first biological pattern and the second biological pattern where textures of those are different each other. In addition, the image processing apparatus 1 includes a normalizing unit 12 which, by using a parameter appropriate to the difference in the textures of the first biological pattern and the second biological pattern, normalizes density of the image on the basis of an average and a standard deviation of pixel values in a local region in the image. The normalizing unit 12 separates the first biological pattern and the second biological pattern in the image by normalizing density of the image. In addition, the image processing apparatus 1 further includes a pattern collating unit 13 including the first collating unit and the second collating unit, which collate known collation patterns with each of the first biological pattern and the second biological pattern which are separated by the normalizing unit 12.

By the above described configuration, the biological patterns can be more efficiently and effectively separated.

Second Embodiment

<Exemplary Configuration of the Image Processing Apparatus According to the Second Embodiment>

An exemplary configuration of the image processing apparatus according to the second embodiment of the present invention will be described with reference to FIG. 2 and FIG. 3. Where, the same reference codes of FIG. 1 are attached to the same functional components as that of the first embodiment.

The image obtaining unit 11 obtains an image of a biological apparatus 22 such as fingers, palms or feet from which it can obtain multiple types of authentication information (e.g. a fingerprint 222 and a blood vessel 221). By light from a light source, the image obtaining unit 11 obtains an image including multiple types of authentication information of the biological apparatus 22 which is a target object for obtaining the image by the image obtaining unit 11. An image processing unit 100 separates the patterns of the multiple types of authentication information by a pattern separating unit 20 which includes the normalizing unit 12 in FIG. 1. According to the example, the image processing unit 100 separates a blood vessel pattern as an example of the first biological pattern and a fingerprint pattern as an example of the second biological pattern. The first collating unit 131 or the second collating unit 132 which are included in the pattern collating unit 13 shown in FIG. 1 compares the respective pattern with a known registered patterns, and judges that it is authenticated when it is coincided and it is not authenticated when it is not coincided. A comparison result outputting unit 30 integrates two collation results with the same weight or different weight, and outputs as an authentication result.

<Exemplary Configuration of the Image Obtaining Unit 11>

Figure 2:
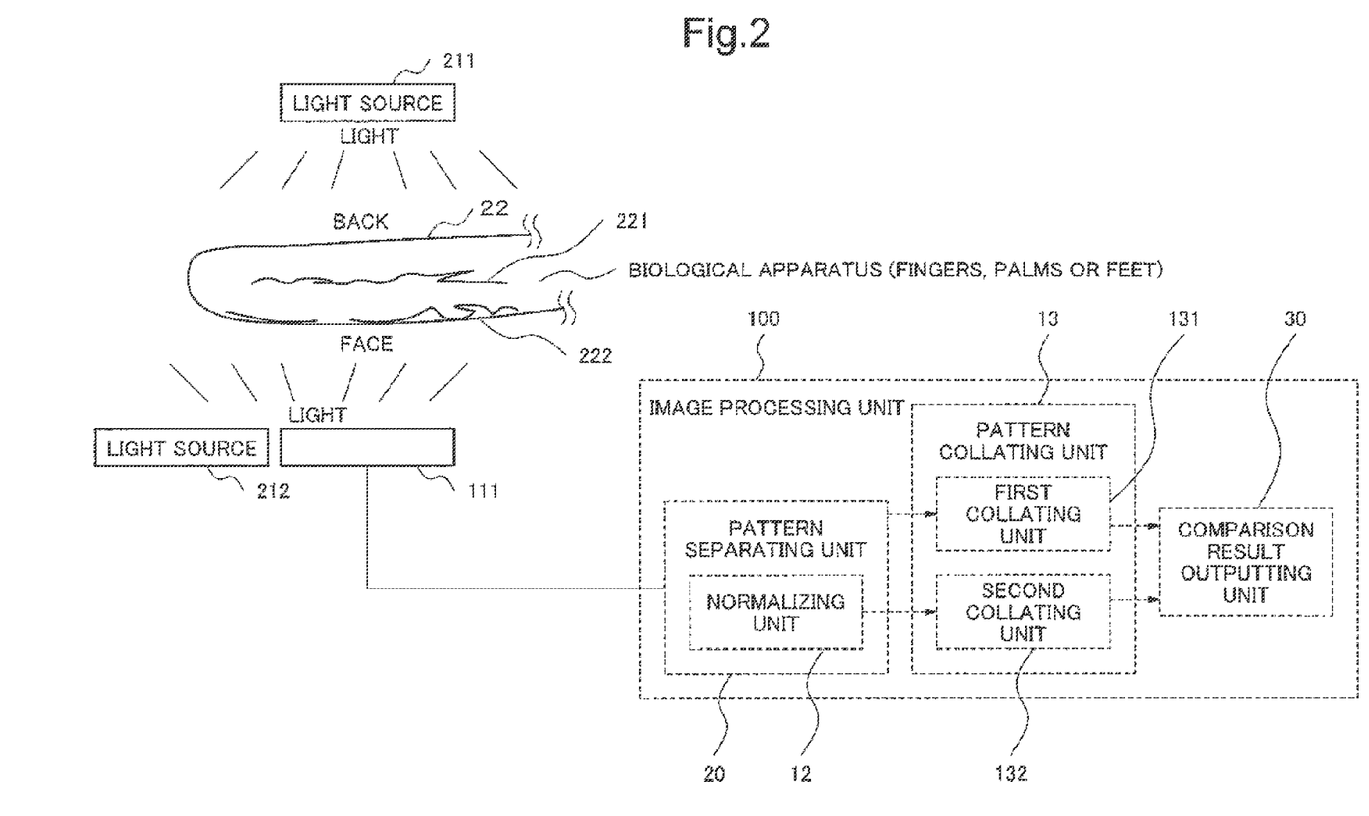
FIG. 2 is a schematic diagram showing a configuration of an image processing apparatus according to the second embodiment of the present invention.

As shown in FIG. 2, the image obtaining unit 11 includes a light source (i.e. a light source 211 and a light source 212) and an image obtaining device 111, or an infrared permeating filter which is used when the light source irradiates near infrared light and is not illustrated. Hereinafter, the respective configuration will be described in detail.

(Example of the Light Source in the Case of Permeated Light and Reflected Light)

It is desirable to use a near infrared LED as the light source according to the present embodiment. The near infrared LED 211 (i.e. the light source 211) is an illumination light source for obtaining the blood vessel image. The near infrared LED 211 should be a LED light source with wavelength of 700 nm to 900 nm considering absorption by hemoglobin. For example, wavelength of the near infrared LED 211 can be wavelength of 830 nm. Further, for example, about four pieces of near infrared LED 211 can be arranged along major axis of the finger to the opposite side of the image obtaining device 111 across a biological apparatus (i.e. in this case, it is a finger) which is a target object for image obtaining. Where, it is possible to suppress unnecessary scattered light and obtain more suitable illumination by arranging a lenticular lens (i.e. semi-cylindrical convex lens) in front of the arranged LED light source so as to tune light to the finger. Thus, it can obtain the blood vessel pattern of a finger, in particular vein patterns which exist a lot around surface of a finger, by installing the light source at a back side of the finger and obtaining an image of the finger by the image obtaining device 111. Hereinafter, a method of arranging the light source to the opposite side of the image obtaining device 111 across the target object and obtaining an image as is mentioned above, is denoted as a permeated light sensing.

On the other hand, the near infrared LED 212 (the light source 212) is an illumination light source for obtaining the fingerprint image. The near infrared LED 212 can be a LED light source with wavelength of near infrared of such as 700 nm to 900 nm. For example, the wavelength of the near infrared LED 212 can also be the same wavelength of 830 nm as a light source for obtaining the blood vessel image. The near infrared LED 212 is arranged as a light source at the same side as the image obtaining device 111 on the basis of a finger which is a target object. The image obtaining device 111 mainly obtains reflected light from a skin surface in the case of obtaining a fingerprint image at this arrangement. In this way, hereinafter, a method of arranging a light source at a face side (i.e. the same side as the image obtaining device 111) of a biological apparatus and obtaining image using a reflected light from the biological apparatus is denoted as a reflected light sensing. For the reflected light sensing, because there is a lot of reflections of the light at ridgelines which are convex parts of skin surface while there is less reflections at valley lines which are concave parts, concerning an image which the image obtaining device 111 obtained, the ridgelines are bright while the valley lines are dark. This is because, at the ridgeline parts of a finger, thickness of epidermis is thick where a blood vessel does not flow and as a result, specular reflections as well as diffuse reflections at the surface are large. On the other hand, at the valley line parts, because thickness of the epidermis is thin and amount of light which permeates to hypodermis which the blood vessel flows is large, it can consider that there is a lot of absorptions and also diffuse reflections are large and specular reflection ingredients are relatively little. For this reason, the near infrared LED 212 should be arranged so as to suppress illumination shading caused by the image obtaining device 111 and local shape of the finger as well as to increase more specular reflections. For example, total of eight LEDs should be arranged in two lines wherein each four pieces formed a line along a major axis of the finger. Following to this kind of arrangement, it can obtain the image in which contrast of the surface patterns caused by the ridgelines of the finger, in other words a fingerprint pattern, is much improved.

(Example of Light Source in Case of Only Reflected Light)

By the way, when installing the near infrared LED 211 for blood vessel illumination of the permeated light sensing, a pedestal which supports the near infrared LED 211 is needed. The apparatus can be shaped so as it inserts a finger in a cover (e.g. in a hole part) which surrounds the pedestal part. Therefore, because the apparatus will become large and an action of inserting a finger in the hole makes oppressive feeling to a user, it is not suitable to apply especially to an ATM terminal. For this reason, it can also adapt the reflected light sensing for obtaining the blood vessel image, and the near infrared LED 211 for blood vessel illumination can be arranged at a side of the image obtaining device 111. Where, in this case, it can change the sensing wavelength to such as wavelength of 760 nm, so that it will be suitable for obtaining the vein image. In this case, in order to permeate frequency band of both 760 nm and 830 nm, the infrared permeating filter can be IR-76 which permeates wavelength of light of no smaller than 760 nm. In addition, when it is more important to reduce influences by ambient light, it can be set the same wavelength to the near infrared LED 211 for obtaining the blood vessel image with the wavelength of the near infrared LED 212 for obtaining the fingerprint image, and arrange a band-pass filter. Further, it can be configured so that the near infrared LED 211 for obtaining the blood vessel image and the near infrared LED 212 for obtaining the fingerprint image are shared and number of components is reduced.

(Example of the Infrared Permeating Filter)

Figure 4:
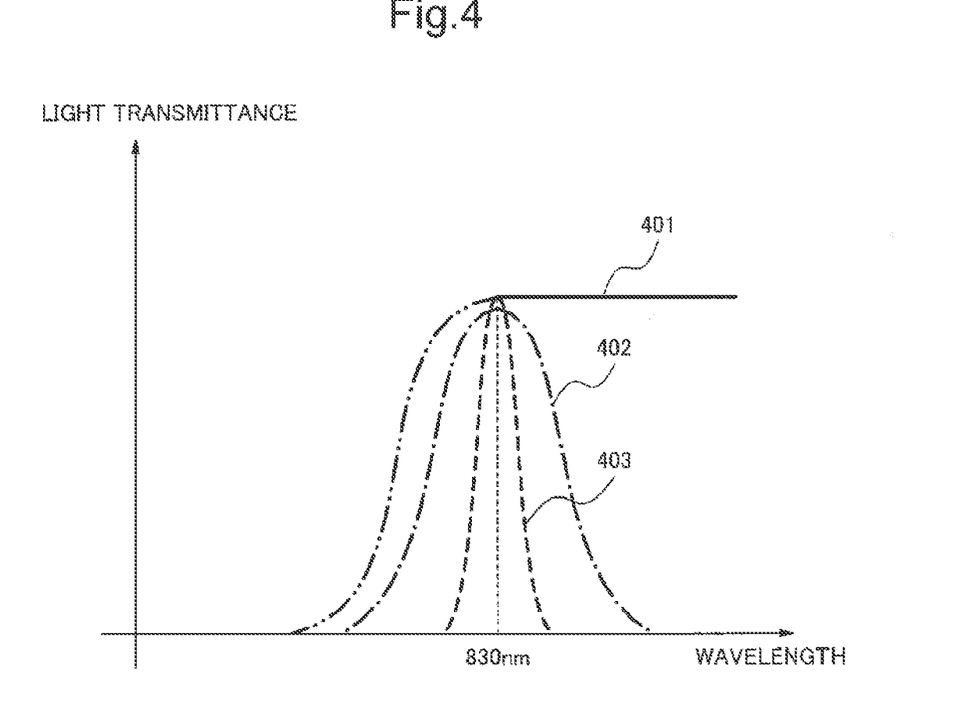
FIG. 4 is a figure describing a filter used by the image processing apparatus according to the second embodiment of the present invention.

Although it is not shown in the figure, in front of the image obtaining device 111 an optical filter (i.e. infrared permeating filter according to the present embodiment) which meets characteristics of the blood vessel pattern and the fingerprint pattern can be installed. This infrared permeating filter can be an IR filter such as IR-83 which is an infrared permeating filter (i.e. IR filter) of permeating wavelength of 830 nm. In the case of the IR-83 filter, threshold wavelength is 830 nm as shown by 401 in FIG. 4. Because light with wavelength shorter than that is hard to permeate IR-83 filter, it can reduce influences by ambient light such as room light or solar light. Further, ambient light can be suppressed by using a band-pass filter which has permeating wavelength of 830 nm. In the case of using a band-pass filter which has a characteristic of the same specific wavelength as the sensing wavelength, it can obtain an image where ambient light is effectively reduced. For example, the infrared permeating filter of RT-830 made by Kenko kougaku Corporation has a permeating characteristic as shown by 402 in FIG. 4, and it can more efficiently suppress ambient light than IR-83 filter. In addition, the band-pass filter by interference shows a sharp band-pass characteristic and it can more efficiently suppress ambient light. In this way, in the case that the sensing wavelength for the fingerprint and the sensing wavelength for the blood vessel are identical, it can efficiently suppress ambient light using the band-pass filter. Where, when using the sensing wavelength of near infrared such as 830 nm, because light permeate into a finger and causes reflection at inside of the finger and absorption at the blood vessel, the blood vessel image of the vein blood vessel is also obtained in addition to reflection at surface of the finger. However, in order to separate each of these patterns from an image in which the fingerprint pattern is superimposed with the blood vessel pattern, it does not need to use different wavelength for the sensing wavelength for obtaining the fingerprint image and the sensing wavelength for obtaining the blood vessel image. Therefore, according to the present embodiment, by using a band-pass filter with single wavelength and sharply narrowed permeating bandwidth, influence by ambient light is efficiently suppressed. The infrared permeating filter can be attached to a lens unit of the image obtaining device 111. In addition, instead of attaching to the image obtaining device 111, the infrared permeating filter can be arranged between the finger, and the near infrared LED 212 and the image obtaining device 111 inside a chassis, in order to protect components such as the near infrared LED 212 and the image obtaining device 111 in the chassis.

(Example of the Image Obtaining Device 111)

The image obtaining device 111 is composed of a two-dimensional image sensing device such as a CCD sensor or a CMOS sensor and a lens. The two-dimensional image sensing device can be an image sensing device which can obtain an image of surface of the finger with resolution of about 500 dpi. For example, in the case that the image obtaining device 111 obtains an image of the finger from a middle phalanx to a distal phalanx with resolution of about 500 dpi or equivalent, the two-dimensional image sensing device can be a device of 1.3 million pixels with size of 1,280×1,024 pixels. In addition, when the image obtaining device 111 obtains only the middle phalanx, the two-dimensional image sensing device can be a device of 0.3 million pixels with size of 640×480 pixels. According to the present embodiment, by using the image sensing device with size of 1,280×1,024 pixels, the image obtaining device 111 obtains an image of a finger from the middle phalanx to the distal phalanx. Where, although the infrared permeating filter is installed outside the image obtaining device 111 following to the above-mentioned description, it may be installed between the two-dimensional image sensing device and the lens (i.e. installed in front of the two-dimensional image sensing device) at inside of the image obtaining device 111. In this case, because size of the filter can be the same size as the two-dimensional image sensing device, size of the filter can be small. In particular, when a relatively expensive filter such as an interference filter is used, it is preferable that the filter is arranged between the two-dimensional image sensing device and the lens. As a filter for protecting components inside the chassis, such as the image obtaining device 111 and the near infrared LED 212, it is preferable that a relatively economical filter such as IR-83 is installed. In order to obtain an image in which the fingerprint pattern and the blood vessel pattern are intermingled (i.e. superimposed) using the image obtaining device 111 having these kind of the configuration, it is preferable to actuate the image obtaining device 111 as follows. That is, the image obtaining device 111 obtains an image of a finger at a moment when the near infrared LED 211 and the near infrared LED 212 are simultaneously lighting. The obtained image is an image in which the blood vessel pattern which is illuminated by an illumination for blood vessels and the fingerprint pattern which is illuminated by an illumination for the fingerprint are superimposed.

Further, the image obtaining device 111 can be composed using a line-sensor type image sensing device which obtains an image of a finger by scanning. The line-sensor type image sensing device is an image sensing device configured using a one-dimensional line sensor or a strip shaped two-dimensional line sensor with a lenticular lens. By using the image sensing device having this kind of shape, the image obtaining device 111 sequentially obtains an image of a part of the finger as one-dimensional partial image or a rectangular partial image. The image obtaining device 111 successively obtains a partial image of the finger by scanning the finger in a direction of crossing at right angle with the scanning direction, and linearly repeating a process at high speed. Then, the image obtaining device 111 integrates the obtained partial images, and composites an image of the whole finger. The image composed in this way will be an image in which the fingerprint pattern and the blood vessel pattern are intermingled (i.e. superimposing), and is similar to the case that it obtains an image using the above-mentioned two-dimensional image sensing device.

<Exemplary Configuration of a Pattern Separating Unit 20-1>

Figure 3:
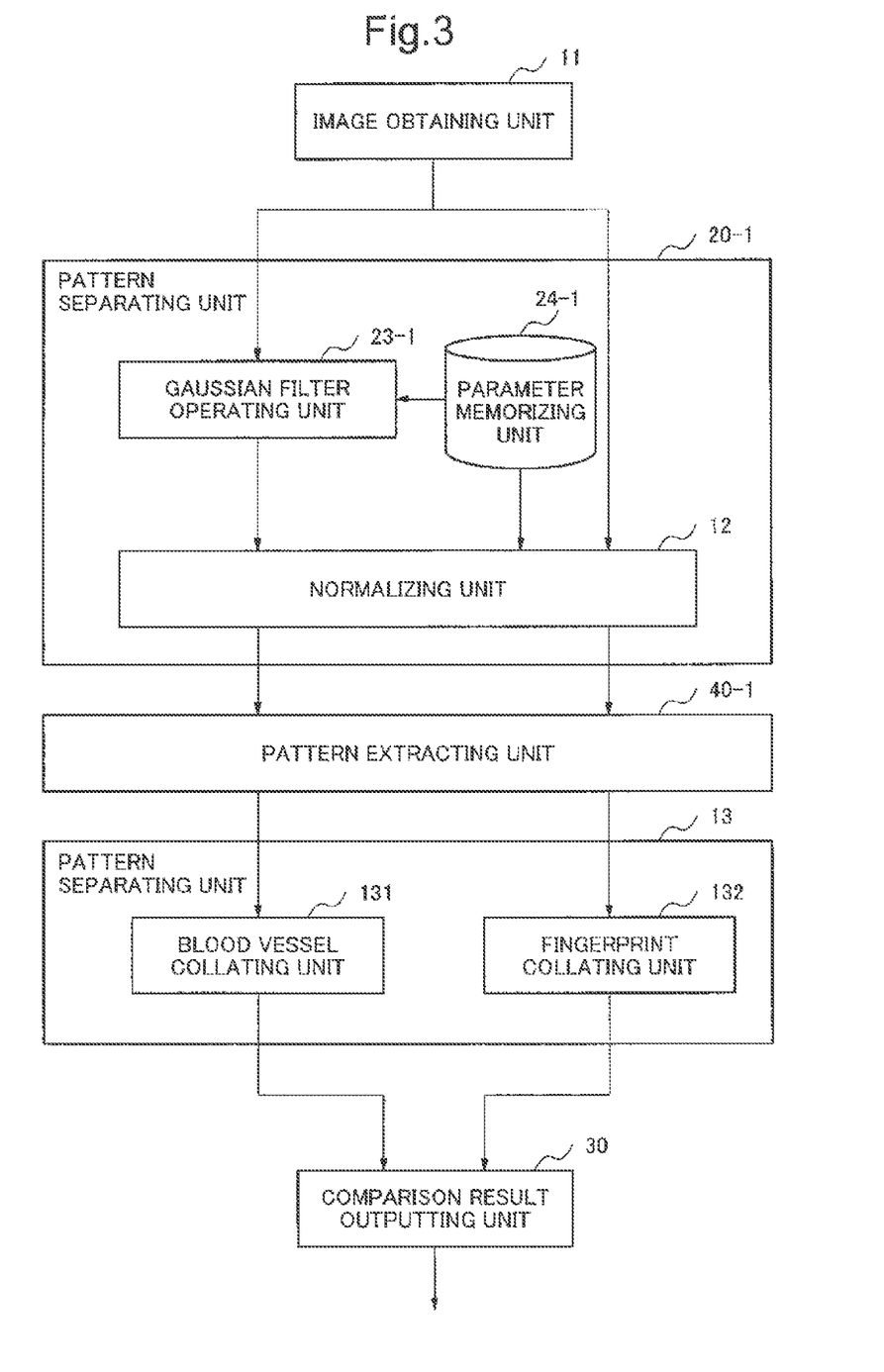
FIG. 3 is a block diagram showing a functional configuration of the image processing apparatus according to the second embodiment of the present invention.

As shown in FIG. 3, the pattern separating unit 20-1 according to the present embodiment includes the following components. Pattern separating unit 20-1 includes a Gaussian filter applying unit 23-1 which applies Gaussian filter to an input image. In addition, the pattern separating unit 20-1 includes the normalizing unit 12 which performs such as a gray level normalization to the image for which Gaussian filter has applied. Further, the pattern separating unit 20-1 includes a parameter memorizing unit 24-1 which memorizes parameters used by the Gaussian filter applying unit 23-1 and parameters used by the normalizing unit 12. Concerning the configuration of FIG. 3, the pattern separating unit 20-1 applies Gaussian filter to an image which is for extracting the blood vessel pattern, and then performs the gray level normalization in the normalizing unit 12. On the other hand, the pattern separating unit 20-1 does not apply Gaussian filter to an image which is for extracting the fingerprint pattern, but performs the gray level normalization in the normalizing unit 12. Based on these procedures, the pattern separating unit 20-1 realizes separation of the patterns. According to the configuration of the present embodiment, it is assumed that the pattern separating unit 20-1 removes a trifling fingerprint pattern from the input image by applying Gaussian filter with a predetermined parameter to the input image, and retains the blood vessel pattern.

(Example of the Gaussian Filter Applying Unit 23-1)

The Gaussian filter applying unit 23-1 applies Gaussian filter, which is a kind of smoothing filters, to the input image and performs filtering. Gaussian filter is a filter of calculating a weighted average by setting a large weight to a pixel near to the target pixel and small weight to a pixel far from the target pixel considering spatial arrangement of the pixels, and performing smoothing of the image. This weight is determined using Gaussian function. A kernel of Gaussian filter is determined using the following formula.

$$k(x, y) = \alpha \times e^{-\frac{(x^2+y^2)}{2\sigma^2}}$$ [Formula 1]

In Formula 1, "x" and "y" are distances from a target pixel, "σ" is a standard deviation value and "α" is a coefficient. In addition, the kernel is a square wherein length of a side is 2×"ksize"+1. Where, "ksize" is a parameter of Gaussian filter. The value of the coefficient "α" is an adjusting value so as total of weight in the kernel calculated by Formula 1 should be one. The Gaussian filter applying unit 23-1 successively applies the kernel of the above calculated Gaussian filter to the target pixel which is positioned at a center position. The Gaussian filter applying unit 23-1 successively selects a target pixel by scanning the image in raster scan order as an example. In other words, the Gaussian filter applying unit 23-1 performs a two-dimensional convolution algorithm process to the input image using Gaussian kernel k (x, y). The parameter memorizing unit 24-1 memorizes the parameter which the Gaussian filter applying unit 23-1 uses. A parameter which the parameter memorizing unit 24-1 memorizes includes a parameter (including whether or not Gaussian filter is applied) for extracting the fingerprint pattern and a parameter for extracting the blood vessel pattern. A specific example of a parameter which the parameter memorizing unit 24-1 memorizes will be described later.

(Example of the Normalizing Unit 12)

The normalizing unit 12 performs the gray level normalization by the following formula on the basis of an average and a standard deviation in a specific range of an image.

$$I'_m = \text{gain} \times \frac{I_m - \langle I_m \rangle}{\sqrt{\langle I_m^2 \rangle - \langle I_m \rangle^2} + \varepsilon} + \text{bias}$$ [Formula 2]

In Formula 2, "gain", "ε" and "bias" are the parameters in the process of the gray level normalization respectively. "Im" is a pixel value of the target pixel. "I'm" is a pixel value of the target pixel after the gray level normalization is performed. "<Im>" is an average value of pixel values in a square area wherein length of a side is (2×size+1) and the target pixel is positioned at a center position. The standard deviation is an index representing scattering state of a value, and {(<Im2>−<Im>2)}½ in Formula 2 is a value of the standard deviation in the square area wherein length of a side is (2×"size"+1) and the target pixel is positioned at a center position. Where, above-mentioned "size" is a parameter of the gray level normalization. The normalizing unit 12 performs the gray level normalization on each pixel. The normalizing unit 12 calculates a pixel value of a target pixel after performed the gray level normalization by Formula 2 within the above-mentioned square area where the target pixel is positioned at a center position. For example, the normalizing unit 12 scans a pixel in an image in a raster scan order, and successively selects a target pixel. The parameter memorizing unit 24-1 memorizes parameters which the normalizing unit 12 uses. The parameters which the parameter memorizing unit 24-1 memorizes include a parameter for extracting the fingerprint pattern and a parameter for extracting the blood vessel pattern.

(Example of the Parameter Memorizing Unit 24-1)

Figure 5:
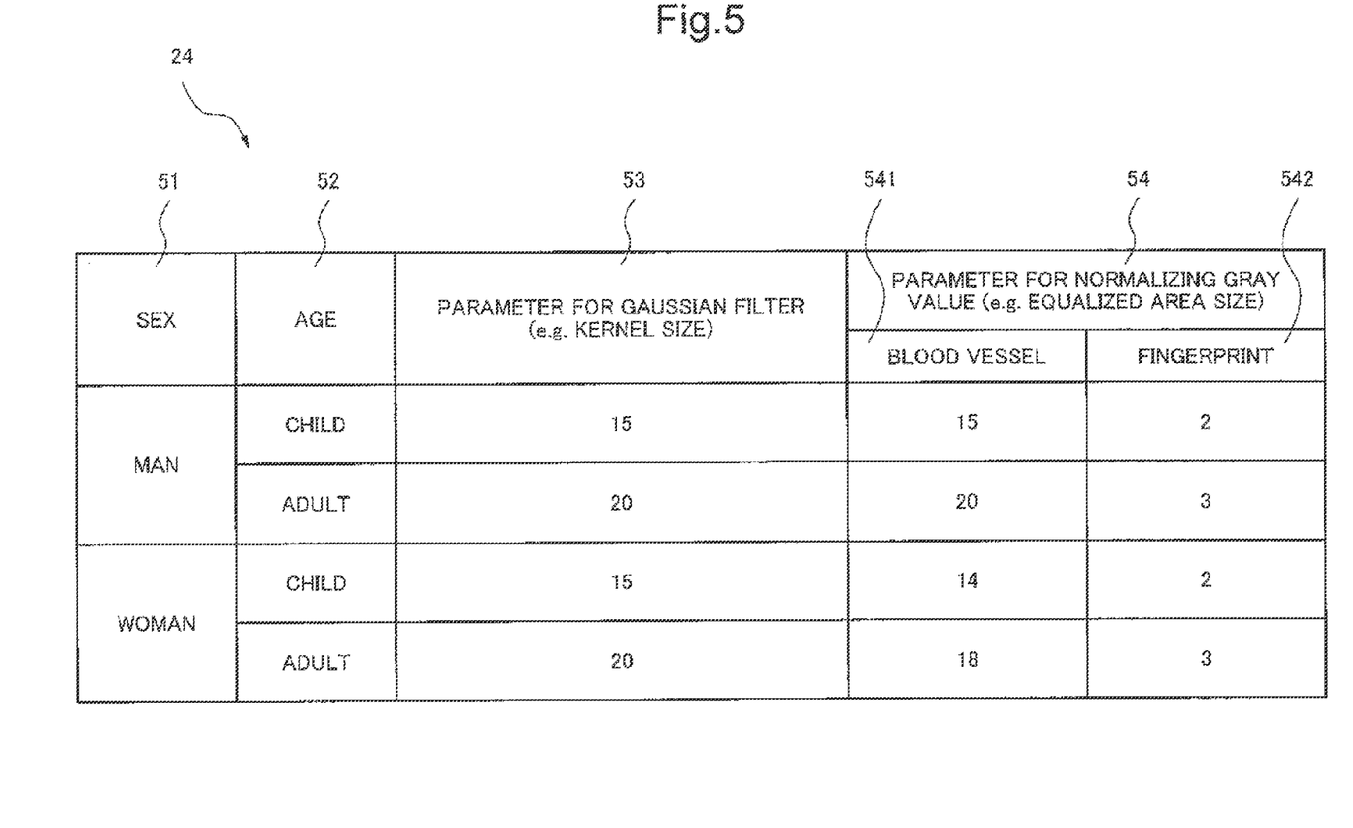
FIG. 5 is a figure describing a parameter database used by the image processing apparatus according to the second embodiment of the present invention.

FIG. 5 is the figure showing an example of the parameters which the parameter memorizing unit 24-1 according to the present embodiment memorizes. In the example of FIG. 5, the parameter memorizing unit 24-1 in advance memorizes parameters including parameters for Gaussian filter and parameters for gray value normalization.

As shown in FIG. 5, as an example of a parameter 53 for Gaussian filter, the kernel size, which is size of one side of a two-dimensional Gaussian filter matrix for processing of each pixel, is indicated. Further, as an example of a parameter 54 for gray value normalization, averaged area size, which is size of one side of a pixel region which is used to calculate an average for normalizing, is indicated. These parameters are selected according to sex 51 (man/woman) and age 52 (child/adult). In addition, a parameter 54 for gray value normalization takes different values when extracting the fingerprint pattern and when extracting the blood vessel pattern from the inputted image, even when the sex and the age are the same. Herewith, it will describe these parameter values.

Where, FIG. 5 shows an example of the parameters when selecting parameters according to sex 51 (man/woman) and age 52 (child/adult). However, a parameter for Gaussian filter and/or a parameter for gray value normalization can be selected according to other characteristics which a living body possesses (i.e. difference in peoples or races), or other characteristics of biological information (i.e. blood vessel pattern or fingerprint pattern). In addition, because of change in the characteristics of the light source and the image obtaining device due to change in power supply voltage, change of the light source and/or the image obtaining device due to substitution or deterioration with age and environment change including temperature, humidity and ambient light, change of the characteristics in the image which the image obtaining device obtains may occur. The parameter for Gaussian filter and/or the parameter for gray value normalization can be selected considering change of characteristics in the image which the image obtaining device obtained.

<Processing Example of the Pattern Separating Unit 20-1>

An example where the pattern separating unit 20-1 separates into the fingerprint pattern and the blood vessel pattern respectively from an image, which the image obtaining unit 11 obtained from an image of, for example, 1,280×1,024 pixels equivalence to 500 dpi to 600 dpi in which the fingerprint pattern and the blood vessel pattern are included, will be described. In the case that a pattern extracting unit 40-1 extracts the fingerprint pattern, the Gaussian filter applying unit 23-1 does not apply Gaussian filter to the image which the image obtaining unit 11 obtained. Then, the normalizing unit 12 sets the parameter "size" of the gray level normalization to a small value such as "3" as shown 542 in FIG. 5, and then the pattern extracting unit 40-1 can extract the fingerprint pattern. When the pattern extracting unit 40-1 extracts the blood vessel pattern, the Gaussian filter applying unit 23-1 applies Gaussian filter to an image which the image obtaining unit 11 obtained, and the normalizing unit 12 performs the gray level normalization. In this case, as shown in 53 and 541 in FIG. 5, the parameter "ksize" of Gaussian filter in the Gaussian filter applying unit 23-1 and the parameter "size" of the gray level normalization in the normalizing unit 12 should be a large values such as "20" respectively. By these processes, the pattern extracting unit 40-1 can extract the blood vessel pattern.

This is because, in the image, the fingerprint pattern has a small texture compared with the blood vessel pattern. Increasing both the kernel size "ksize" of Gaussian filter and the value of the standard deviation "a" brings an effect that it enhances effect of gradations and fades small pattern in the texture. Based on the effect, the Gaussian filter applying unit 23-1 can delete the fingerprint pattern and leave the blood vessel pattern. In addition, the process of the gray level normalization of the normalizing unit 12 brings an effect that it equalizes the average and the standard deviation of pixel values in a local range of the image. Further, similar to Gaussian filter, the gray level normalization by the normalizing unit 12 also brings an effect that it can delete or leave the pattern according to fineness of the texture <Configuration and Process Example of the Pattern Extracting Unit 40-1>

The pattern extracting unit 40-1 extracts branch points and end points of veins, which are included in the image for which Gaussian filter and the gray level normalization have performed, as the characteristic points of the blood vessel pattern. On the other hand, the pattern extracting unit 40-1 extracts branch points and end points of ridgelines, which are included in the image for which Gaussian filter has not performed but the gray level normalization has performed, as the characteristic points of the fingerprint pattern. As is described above, the pattern extracting unit 40-1 can extract the fingerprint pattern and the blood vessel pattern by processes of Gaussian filter and the gray level normalization. Where, because the processes in the pattern extracting unit 40-1 are not the main elements of the present invention, the detailed descriptions are omitted.

<Configuration and Process Example of the Pattern Collating Unit 13>

For each of the blood vessel pattern and the fingerprint pattern which are extracted and separated by the above-mentioned method, a blood vessel collating unit 131 performs collating with pre-registered characteristics of the blood vessel pattern and obtains a blood vessel collation result, and a fingerprint collating unit 132 performs collating with pre-registered characteristics of the fingerprint pattern and obtains a fingerprint collation result. Where, because the processes in the pattern collating unit 13 are not the main elements of the present invention, the detailed descriptions is omitted.

<Configuration and Process Example of the Comparison Result Outputting Unit 30>

The comparison result outputting unit 30, according to reliability of the authentication of blood vessel collation and fingerprint collation, sets weight to the collation results and integrates the collation results, and outputs as a last collation result (i.e. authentication result). Where, because the processes in the comparison result outputting unit 30 are not the main elements of the present invention, the detailed descriptions are omitted.

<Operational Example of the Image Processing Apparatus According to the Second Embodiment>

Figure 6:
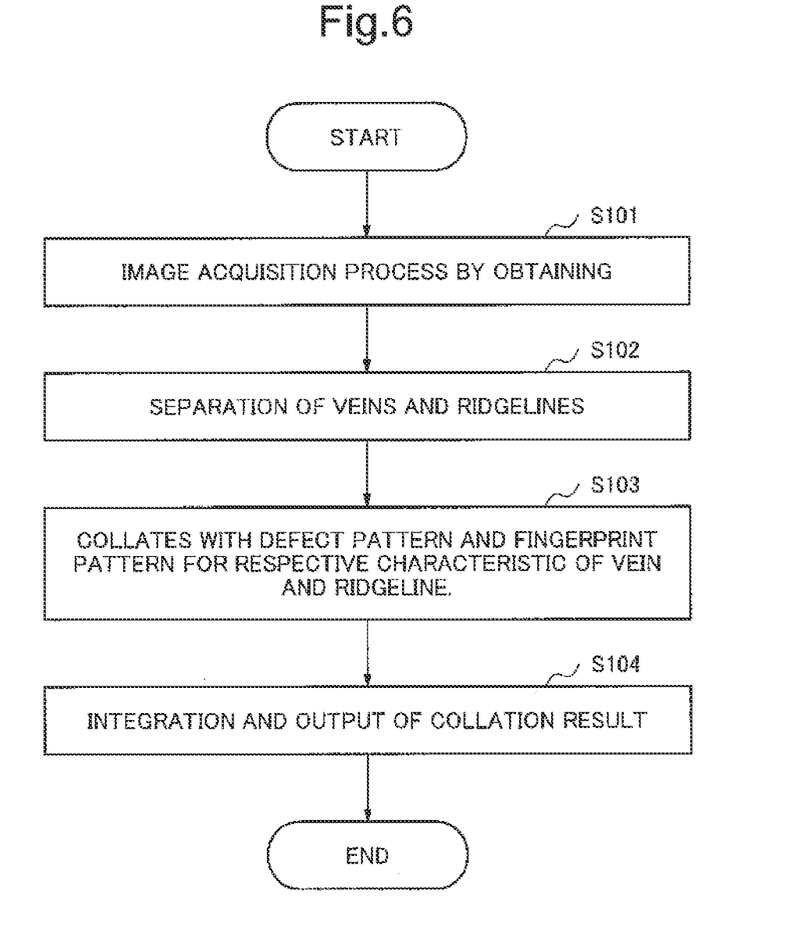
FIG. 6 is a flowchart showing a flow of process executed by the image processing apparatus according to the second embodiment of the present invention.

FIG. 6 is the flowchart showing an example of operation procedure of the image processing apparatus according to the second embodiment. This flowchart corresponds to an image processing program which is executed by a CPU in a computer, when the image processing apparatus in FIG. 3 is realized by the computer which executes according to programs.

At first, in Step S101, the CPU instructs to obtain an image to the image obtaining unit 11, and obtains an image which the image obtaining device 111 obtained. Then, in Step S102, by a combination of Gaussian filter and the gray level normalization, the CPU separates (i.e. emphasizes or eliminates one from the image) the vein which is the blood vessel pattern and the ridgeline which is the fingerprint pattern in the image. In Step S103, the CPU performs collation of the characteristics of the vein, which is the blood vessel pattern, with the blood vessel pattern which is registered in advance, and collates the characteristics of the ridgeline, which is the fingerprint pattern, with the fingerprint pattern which is registered in advance. In Step S104, the CPU summarizes the collation results in Step S103, and outputs the final result of the authentication.

According to the present embodiment, by separating and extracting the fingerprint pattern and the blood vessel pattern using Gaussian filter and the gray level normalization, there is an effect that the noise resisting extraction and separation becomes available.

Third Embodiment

According to the second embodiment, the pattern separating unit 20-1 does not apply Gaussian filter to an image from which the fingerprint pattern is extracted. However, when there exists, on biological surface or inside of it, a pattern whose texture is smaller than that of a fingerprint, or when a noise of frequency smaller than that of a fingerprint is superimposed due to problems of an apparatus or influences of surrounding environment, it is also effective to apply Gaussian filter to the image which is for extracting the fingerprint pattern.

<Configuration and Process Example of the Image Processing Apparatus According to the Third Embodiment>

Figure 7:
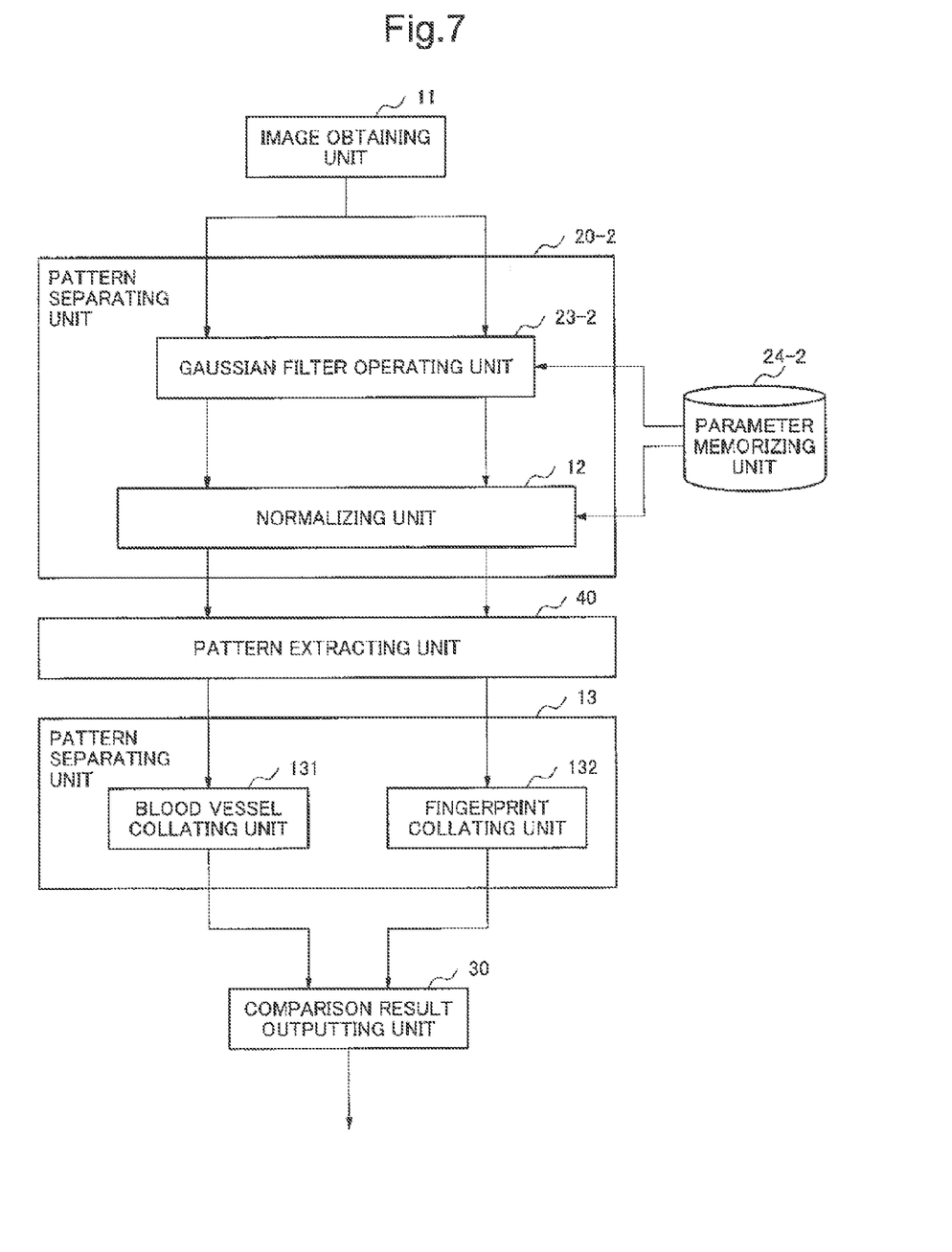
FIG. 7 is a block diagram showing a functional configuration of an image processing apparatus according to the third embodiment of the present invention.

In FIG. 7, the exemplary configuration of the image processing apparatus according to the third embodiment is shown. Concerning the configuration of the image processing apparatus according to the third embodiment, a point of difference from the second embodiment is that a Gaussian filter applying unit 23-2 also applies Gaussian filter to an image which is for extracting the fingerprint pattern. For that purpose, the parameter memorizing unit 24-2 is memorizing parameters of Gaussian filter for the image from which the fingerprint pattern is extracted. When the case of the kernel size in FIG. 5 is taken as an example, the parameter can be a small value such as "1" to "3" with which a texture smaller than the fingerprint pattern can be removed. Alternatively, other parameters for Gaussian filter can be considered. Because a pattern separating unit 20-2 includes the Gaussian filter applying unit 23-2, the pattern separating unit 20-2 is substituted with the pattern separating unit 20-1 according to the second embodiment.

The processes according to the third embodiment is basically the same as that according to the second embodiment other than a process in which the Gaussian filter applying unit 23-2 also applies Gaussian filter to the image from which the fingerprint pattern is extracted.

Fourth Embodiment

According to the second embodiment, even if there is a problem with the result of the pattern extraction and the pattern collation, only re-input with the same condition or re-adjustment of the apparatus by hand are enabled. On the other hand, the image processing apparatus according to the fourth embodiment automatically adjusts parameters appropriately by a feeding back the result of the pattern extraction and the pattern collation.

<Configuration and Process Example of the Image Processing Apparatus According to the Fourth Embodiment>

Figure 8:
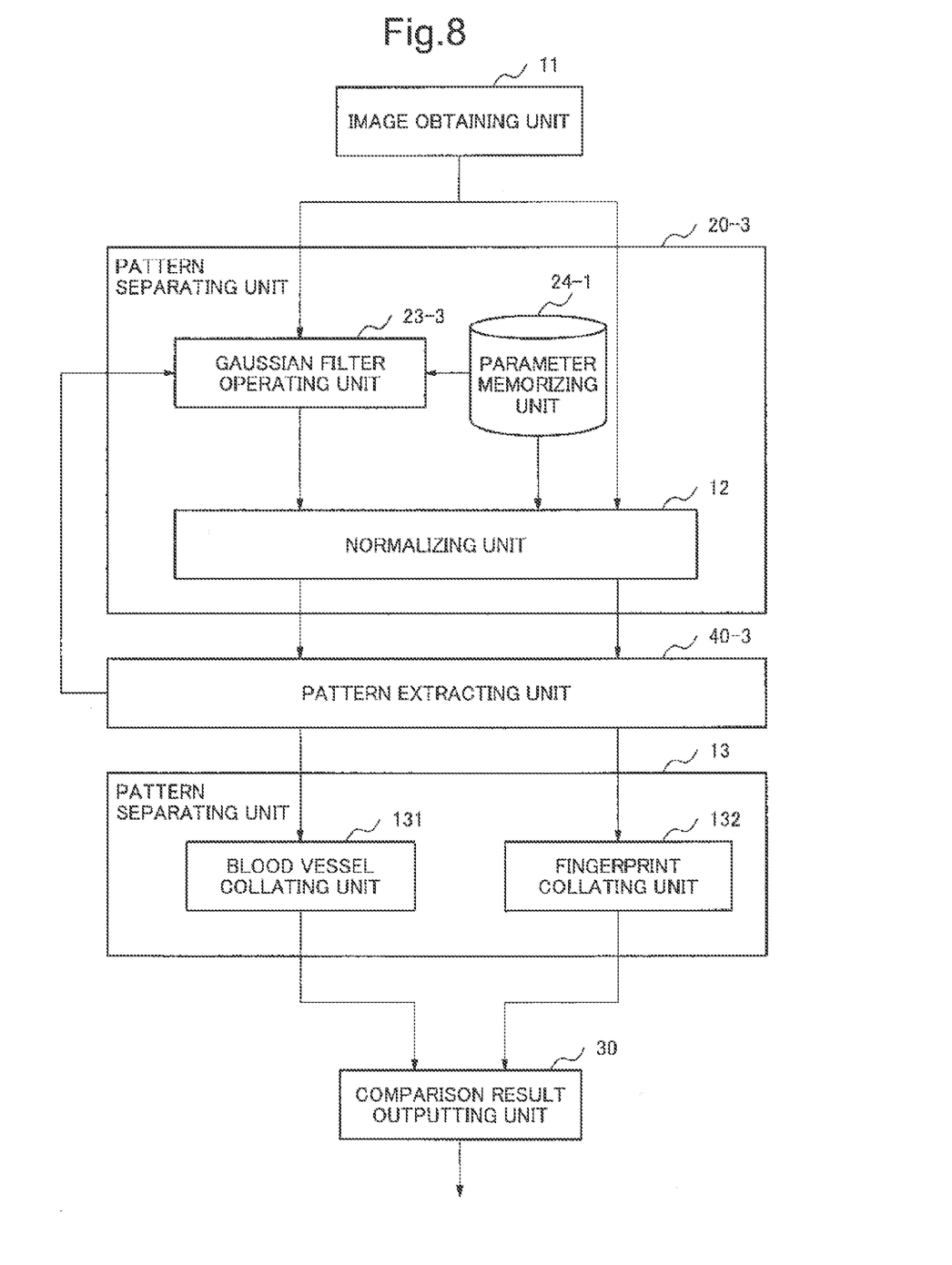
FIG. 8 is a block diagram showing a functional configuration of an image processing apparatus according to the fourth embodiment of the present invention.

In FIG. 8, the exemplary configuration of the image processing apparatus according to the fourth embodiment is shown. Concerning the configuration of the image processing apparatus according to the fourth embodiment, a point of difference from the second embodiment is that, when there are problems with the extraction result in a pattern extracting unit 40-3, modification of the parameter of a Gaussian filter applying unit 23-3 and a more certain pattern extraction are performed. For that purpose, the pattern extracting unit 40-3 includes a component which evaluates the result of the pattern extraction. For example, as a result that the pattern extracting unit 40-3 evaluates the result of the pattern extraction, if the result of the pattern extraction shows that the blood vessels are not connected each other, a bilateral lines of the blood vessel are not even, the blood vessels are too thick or improbable characteristic points (i.e. branch points or end points) are included, then the Gaussian filter applying unit 23-3 changes the parameters. According to the fourth embodiment, the pattern extracting unit 40-1 and the Gaussian filter applying unit 23-1 according to the second embodiment are substituted with the pattern extracting unit 40-3 and the Gaussian filter applying unit 23-3 respectively.

The processes according to the fourth embodiment is basically the same as that according to the second embodiment other than a point that the result of the pattern extracting unit 40-3 is fed back to the parameter of the Gaussian filter applying unit 23-3.

Where, the feedback of the extraction result in the pattern extracting unit 40-3 according to the fourth embodiment can be applied to a case where there is a problem with an extraction result of the fingerprint pattern in the third embodiment. In the case of the fingerprint pattern, the pattern extracting unit 40-3 should evaluate that there is a problem when, in particular, recognizing that there exits disconnections of the ridgelines, extraordinary thin ridgelines or contact of the ridgelines in the fingerprint pattern.

In addition, in the pattern collating unit 13, when the other pattern is not collated even though a pattern is collated, the Gaussian filter applying unit 23-3 can separates a pattern which is not collated by changing the parameters.

Further, the pattern extracting unit 40-3 can feed back the pattern extraction to the parameters of the normalizing unit 12. Furthermore, the pattern extracting unit 13 can heed back the collation result to the parameters of the normalizing unit 12.

Other Embodiments

While having described in detail the embodiments of the present invention, systems or apparatuses which are any combinations of respective characteristic included in each embodiment are within the scope of the present invention.

In addition, the present invention can be applied to any systems configured by a plurality of devices and also can be applied to a stand-alone apparatus. Further, the present invention can be applied to a case where software, by which the function of the embodiment is realized, is supplied directly or from a remote to a system or to an apparatus. Accordingly, the scope of the invention of the present application also includes an image processing program which will be installed in the computer in order to realize the functions of the present invention by a computer, or a recording media which stored the image processing program and a WWW server which enables to download the image processing program.

Another Expressions of Embodiments

Although it can also be described by the following supplementary notes, a part or whole of the above-mentioned embodiments are not limited by the followings.

(Supplementary Note 1)

An image processing apparatus for authenticating a biological pattern which a biological apparatus has, characterized by comprising:

an image obtaining means for obtaining an image in which a first biological pattern and a second biological pattern having different textures are superimposed;

a normalizing means for normalizing density of the above-mentioned image on the basis of an average and a standard deviation of pixel values inside a local region in the above-mentioned image using a parameter in accordance with difference in texture between the above-mentioned first biological pattern and the above-mentioned second biological pattern to thereby separate the above-mentioned first biological pattern and the above-mentioned second biological pattern in the above-mentioned image; and a pattern collating means for collating a known pattern for collation with each of the above-mentioned first biological pattern and the above-mentioned second biological pattern separated by the above-mentioned normalizing means.

(Supplementary Note 2)

The image processing apparatus according to Supplementary Note 1, characterized in that the above-mentioned first biological pattern is a blood vessel pattern and the above-mentioned second biological pattern is a fingerprint.

(Supplementary Note 3)

The image processing apparatus according to Supplementary Notes 1 or 2, characterized by further comprising:

a filtering means for filtering the above-mentioned image obtained by the above-mentioned image obtaining means using Gaussian filter; wherein the above-mentioned normalizing means normalizes density of an image filtered by the above-mentioned filtering means.

(Supplementary Note 4)

The image processing apparatus according to Supplementary Notes 1 or 2, characterized by further comprising:

a filtering means for filtering the above-mentioned image obtained by the above-mentioned image obtaining means using Gaussian filter; wherein the above-mentioned normalizing means normalizes density of an image before filtered by the above-mentioned filtering means and also normalizes density of an image after filtered by the above-mentioned filtering means.

(Supplementary Note 5)

The image processing apparatus according to any one of Supplementary Notes 1 to 4, characterized in that the above-mentioned image obtaining means irradiates light from both of face side and back side to a biological apparatus and simultaneously obtains the above-mentioned first biological pattern which exists inside of the above-mentioned biological apparatus and the above-mentioned second biological pattern which exists at a surface of the face side of the above-mentioned biological apparatus.

(Supplementary Note 6)

The image processing apparatus according to any one of Supplementary Notes 1 to 5, characterized by further comprising:

a memory means for storing as the above-mentioned parameter each of the first parameter and the second parameter correspond respectively to the above-mentioned first biological pattern and the above-mentioned second biological pattern.

(Supplementary Note 7)

The image processing apparatus according to any one of Supplementary Notes 1 to 6, characterized in that the above-mentioned parameter is size of the above-mentioned local region.

(Supplementary Note 8)

The image processing apparatus according to any one of Supplementary Notes 1 to 7, characterized in that the above-mentioned image obtaining means obtains the above-mentioned image using an optical filter appropriate to the above-mentioned first biological pattern and the above-mentioned second biological pattern.

(Supplementary Note 9)

An image processing method for authenticating a biological pattern which a biological apparatus has, characterized by comprising:

an obtaining step for obtaining an image in which a first biological pattern and a second biological pattern having different textures are superimposed;

a normalizing step for normalizing density of the above-mentioned image on the basis of an average and a standard deviation of pixel values inside a local region in the above-mentioned image using a parameter in accordance with difference in texture between the above-mentioned first biological pattern and the above-mentioned second biological pattern to thereby separate the above-mentioned first biological pattern and the above-mentioned second biological pattern in the above-mentioned image; and a pattern collating step for collating a known pattern for collation with each of the above-mentioned first biological pattern and the above-mentioned second biological pattern separated by the above-mentioned normalizing step.

(Supplementary Note 10)

An image processing program for authenticating a biological pattern which a biological apparatus has, characterized by making a computer operate as:

an obtaining step for obtaining an image in which a first biological pattern and a second biological pattern having different textures are superimposed;

a normalizing step for normalizing density of the above-mentioned image on the basis of an average and a standard deviation of pixel values inside a local region in the above-mentioned image using a parameter in accordance with difference in texture between the above-mentioned first biological pattern and the above-mentioned second biological pattern to thereby separate the above-mentioned first biological pattern and the above-mentioned second biological pattern in the above-mentioned image; and a pattern collating step for collating a known pattern for collation with each of the above-mentioned first biological pattern and the above-mentioned second biological pattern separated by the above-mentioned normalizing step.

While having described the present invention referring to the embodiments, the present invention is not limited to the above mentioned embodiments. It is to be understood that to the configurations and details of the present invention, various changes can be made within the scope of the present invention by those skilled in the arts.

This application is based upon and claims the benefit of priority from Japanese patent application No. 2010-180730, filed on Aug. 12, 2010, the disclosure of which is incorporated herein in its entirety by reference.

DESCRIPTION OF THE CODES 1 image processing apparatus
11 image obtaining unit 12 normalizing unit
13 pattern collating unit
20, 20-1, 20-2 or 20-3 pattern separating unit
22 biological apparatus
23-1, 23-2 or 23-3 Gaussian filter applying unit
24, 24-1 or 24-2 parameter memorizing unit
30 comparison result outputting unit
40, 40-1 or 40-3 pattern extracting unit
51 sex age
53 parameter for Gaussian filter
54 parameter for gray value normalization
100 image processing unit
111 image obtaining device
131 blood vessel collating unit (first collating unit)
132 fingerprint collating unit (second collating unit)
211 or 212 light source (near infrared LED)
221 blood vessel
222 fingerprint
541 parameter for gray value normalization (blood vessel)
542 parameter for gray value normalization (fingerprint)

The invention claimed is:

1. An image processing apparatus, characterized by comprising:
    an image obtaining unit which obtains an image in which a first biological pattern and a second biological pattern having different textures are superimposed;
    a normalizing unit which normalizes density of said image on the basis of an average and a standard deviation of pixel values inside a local region in said image using the size of said local region and at least one other parameter in accordance with difference in texture between said first biological pattern and said second biological pattern to thereby separate said first biological pattern and said second biological pattern in said image; and
    a pattern collating unit which collates a known pattern for collation with each of said first biological pattern and said second biological pattern separated by said normalizing unit
    wherein said first biological pattern is a blood vessel pattern and said second biological pattern is a fingerprint.

2. The image processing apparatus according to claim 1, characterized by further comprising:
    a filtering unit which filters said image obtained by said image obtaining unit using Gaussian filter; wherein
    said normalizing unit normalizes density of an image filtered by said filtering unit.

3. The image processing apparatus according to claim 1, characterized by further comprising:
    a filtering unit which filters said image obtained by said image obtaining unit using Gaussian filter; wherein
    said normalizing unit normalizes density of an image before filtered by said filtering unit and also normalizes density of an image after filtered by said filtering unit.

4. The image processing apparatus according to claim 1, characterized in that
    said image obtaining unit irradiates light from both of face side and back side to a biological apparatus and simultaneously obtains said first biological pattern which exists inside of said biological apparatus and said second biological pattern which exists at a surface of the face side of said biological apparatus.

5. The image processing apparatus according to claim 1, characterized by further comprising:
    a memory unit which stores as said parameter a first parameter and a second parameter correspond respectively to said first biological pattern and said second biological pattern.

6. The image processing apparatus according to claim 1, characterized in that
    said parameter is size of said local region.

7. The image processing apparatus according to claim 1, characterized in that
    said image obtaining unit obtains said image using an optical filter appropriate to said first biological pattern and said second biological pattern.

8. An image processing method, characterized in that
    obtaining an image in which a first biological pattern and a second biological pattern having different textures are superimposed,
    normalizing density of said image on the basis of an average and a standard deviation of pixel values inside a local region in said image using the size of said local region and at least one other parameter in accordance with difference in texture between said first biological pattern and said second biological pattern to thereby separate said first biological pattern and said second biological pattern in said image, and
    collating a known pattern for collation with each of said first biological pattern and said second biological pattern separated by said normalizing unit;
    wherein said first biological pattern is a blood vessel pattern and said second biological pattern is a fingerprint.

9. A recording medium for storing an image processing program, characterized by a computer for executing:
    an image obtaining unit which obtains an image in which a first biological pattern and a second biological pattern having different textures are superimposed;
    a normalizing unit which normalizes density of said image on the basis of an average and a standard deviation of pixel values inside a local region in said image using the size of said local region and at least one other parameter in accordance with difference in texture between said first biological pattern and said second biological pattern to thereby separate said first biological pattern and said second biological pattern in said image; and
    a pattern collating unit which collates a known pattern for collation with each of said first biological pattern and said second biological pattern separated by said normalizing unit;
    wherein said first biological pattern is a blood vessel pattern and said second biological pattern is a fingerprint.

10. An image processing apparatus, characterized by comprising:
    an image obtaining means for obtaining an image in which a first biological pattern and a second biological pattern having different textures are superimposed;
    a normalizing means for normalizing density of said image on the basis of an average and a standard deviation of pixel values inside a local region in said image using the size of said local region and one or more other parameters in accordance with difference in texture between said first biological pattern and said second biological pattern to thereby separate said first biological pattern and said second biological pattern in said image; and
    a pattern collating means for collating a known pattern for collation with each of said first biological pattern and said second biological pattern separated by said normalizing means;
    wherein said first biological pattern is a blood vessel pattern and said second biological pattern is a fingerprint.

* * * * *